United States Patent [19]

Grayson et al.

[11] Patent Number: 6,069,255
[45] Date of Patent: May 30, 2000

[54] PREPARATION OF VINYL ISOTHIOCYANATES

[75] Inventors: James Ian Grayson; Graham Heyes, both of Durham; Arthur Jackson, Washington; James Orrock Macgregor, Co Durham; Brian John Somerville, Cleveland, all of United Kingdom

[73] Assignee: Laporte Industries, Limited, London, United Kingdom

[21] Appl. No.: 09/088,836

[22] Filed: Jun. 2, 1998

[30] Foreign Application Priority Data

Jun. 14, 1997 [GB] United Kingdom .................... 9712409

[51] Int. Cl.⁷ .................................................. C07D 277/20
[52] U.S. Cl. ............................................ 548/202; 548/205
[58] Field of Search ....................................... 548/202, 205

[56] References Cited

U.S. PATENT DOCUMENTS 5,180,833  1/1993  Uneme et al. .......................... 548/202

*Primary Examiner*—John M. Cooney, Jr.
*Attorney, Agent, or Firm*—Rodman and Rodman

[57] ABSTRACT

A process for preparing a vinyl isothiocyanate comprises contacting a halogen-substituted allyl thiocyanate, in solution and at an elevated temperature, with an acidic material which is either an acid or a halide or oxyhalide of an inorganic acid. The halogen-substituted allyl thiocyanate may be prepared from a dihalogenated alkene. The vinyl isothiocyanate may subsequently be converted to a thiazole.

19 Claims, No Drawings

PREPARATION OF VINYL ISOTHIOCYANATES

The present invention relates to the preparation of vinyl isothiocyanates and is an improved process for that purpose.

Substituted vinyl isothiocyanates are useful intermediates in the preparation of substituted thiazoles. These latter compounds may in turn be important intermediates in the manufacture of agrochemical and pharmaceutical products. By way of example, we have described in Patent Specification No. GB 2305172A a process for preparing thiazoles substituted by a haloalkyl group in the 5 position, which entails reacting a halo-substituted vinyl isothiocyanate in solution with a chlorinating or brominating agent.

These halo-substituted vinyl isothiocyanates are more attractive starting materials for the preparation of the desired thiazoles than previously-proposed starting materials in that they may be more readily available. They may be prepared by a method described by K. Schulze et al in Journal fuer Praktische Chemie, 1980, Vol. 322 at pages 629–637, which method entails reacting a dihalogenated alkene, for example 1,3-dichloropropene, with an alkali metal thiocyanate or ammonium thiocyanate.

The foregoing process of Schulze et al takes place in two stages, involving firstly the formation of an allyl thiocyanate and then, in a separate second stage, the thermal rearrangement of the allyl thiocyanate to the desired vinyl isothiocyanate. Unfortunately this process displays several disadvantages. First of all, the overall yield of vinyl isothiocyanate is low, for example as little as 35 percent based on the quantity of the alkene starting material. Secondly, the second stage uses the toxic solvent dioxan. Attempts to replace the dioxan with less toxic hydrocarbons or chlorinated hydrocarbons as the solvent have led to product of low purity and a significant formation of undesired side products.

Against the foregoing background, it is an object of the present invention to provide an improved process for the conversion of halogen-substituted allyl thiocyanates to the corresponding vinyl isothiocyanates.

The process according to the present invention comprises contacting a halogen-substituted allyl thiocyanate, in solution and at an elevated temperature, with an acidic material which is either an acid or a halide or oxyhalide of an inorganic acid.

The process is of particular advantage in carrying out the two-stage conversion of a dihalogenated alkene to a vinyl isothiocyanate. Thus the invention includes a two-stage process of this type which comprises reacting a dihalogenated alkene of the general formula $$Hal.CH(R_1).CH=C(R_2).Hal$$

wherein the symbols Hal each represents a chlorine or bromine atom, which may be the same or different, and the symbols $R_1$ and $R_2$ each represents a hydrogen atom or an alkyl group containing from 1 to 3 carbon atoms, with an alkali metal thiocyanate or with ammonium thiocyanate, and contacting the halogen-substituted allyl thiocyanate so obtained, in solution and at an elevated temperature, with an acidic material which is either an acid or a halide or oxyhalide of an inorganic acid. The allyl thiocyanate which is the intermediate in this two-stage reaction has the general formula $$NCS.CH(R_1).CH=C(R_2).Hal$$

and, by thermal rearrangement in the presence of the specified acidic material, this compound is converted to the desired vinyl isothiocyanate of the general formula $$Hal.CH(R_1).CH=C(R_2).NCS$$

in both of which general formulae the symbols Hal, $R_1$ and $R_2$ have the meanings given above.

Thus, in its simplest form, as applied to the two-stage production of a vinyl isothiocyanate, the process comprises reacting 1,3-dichloropropene with an alkali metal thiocyanate, for example sodium thiocyanate, and contacting the 1-chloro allyl thiocyanate so produced, in solution and at an elevated temperature, with the acidic material, whereby to obtain 3-chloro-prop-1-enyl isothiocyanate.

The acidic material in the presence of which the thermal rearrangement of the halogen-substituted allyl thiocyanate is effected in the process according to the present invention may be a mineral acid, for example hydrochloric, sulphuric or nitric acid, or an organic acid, for example an aliphatic acid of general formula $R_3$.COOH in which the symbol $R_3$ represents an alkyl group containing 1 to 3 carbon atoms. In a particularly preferred form of the invention, the acid is an organic sulphonic acid, for example methanesulphonic acid or p-toluenesulphonic acid. The acidic material may alternatively be a halide or oxyhalide of an inorganic acid. Among such materials, thionyl chloride and phosphorus oxychloride have proved to be particularly effective.

The acidic material preferably is added in an amount equal to between 1 and 25 mole percent of the allyl thiocyanate, more preferably between 1 and 10 mole percent.

The thermal rearrangement of the allyl thiocyanate is carried out in solution. A wide range of solvents are suitable for this purpose. Such solvents include aliphatic, cycloaliphatic and aromatic hydrocarbons, for example heptane, cyclohexane or toluene, and chlorinated hydrocarbons, for example 1,2-dichlorethane, 1,1,2-trichloroethane or chlorobenzene. The chlorinated hydrocarbons are particularly preferred solvents if the vinyl isothiocyanate prepared by the process of the present invention is to be further reacted to form a thiazole as discussed above, in that the solvent may also be the solvent for this further reaction, thus enabling the isothiocyanate to be reacted without first being isolated from the solvent.

The process according to the present invention for rearrangement of the allyl thiocyanate is conducted at an elevated temperature. For example temperatures within the range from 50° to 150° C. may be used. The selected temperature should take account of the solvent in which the reaction is carried out but reaction temperatures within the range from 80° to 130° C. are preferred.

The halogen-substituted vinyl isothiocyanate prepared by the method according to the present invention may be isolated from the reaction mixture and purified if desired. The isolation and such purification may be carried out by conventional methods, for example by distillation. However, the yields of isothiocyanate achievable by means of the present process are such that, if the solvent chosen is compatible with the requirements of any subsequent reaction, the isothiocyanate may be further reacted as described above without first requiring to be isolated from the reaction mixture.

A further important advantage of the present invention is that, surprisingly, the ratio of the trans-isomer to the cis-isomer of the vinyl isothiocyanate obtained by the process is significantly higher than would otherwise be expected and significantly favours the trans-isomer. Thus the ratio of trans-isomer to cis-isomer in the product may exceed 2:1 or 3:1. When the vinyl isothiocyanate is subsequently to be converted to a thiazole by reacting with a chlorinating or brominating agent, the trans-isomer reacts more readily, so the present process has the advantage of producing a particularly advantageous starting material for that subsequent conversion.

The invention will now be further described with reference to the following Examples, which illustrate, by way of example only, the preparation of 3-chloro-prop-1-enyl isothiocyanate by the process according to the present invention.

EXAMPLE 1

Crude 3-chloroallyl thiocyanate was prepared by reaction of 100 g of 1,3-dichloropropene and 110 g of sodium thiocyanate in 200 ml. of water. The product was separated by extraction into 300 ml. of 1,2-dichloroethane, giving a solution of the thiocyanate of about 24 percent concentration.

To the solution of the thiocyanate, 5.0 g (3 mole percent) of p-toluenesulphonic acid was added and the solution was subjected to azeotropic distillation until all residual water had been removed. The solution was placed in an autoclave and the thermal rearrangement was carried out by heating the solution to 110° C. for 12 hours.

The resulting isothiocyanate solution was filtered through a bed of charcoal and yielded 460 g of a clear yellow solution of 3-chloro-prop-1-enyl isothiocyanate. GC analysis showed that the product comprised 87 percent of this compound in the form of a mixture of trans- and cis-isomers in the ratio 2.2:1, together with just 4 percent of unconverted dichloropropene and 7 percent of 1,3-bis (isothiocyanato) propenes.

COMPARATIVE EXAMPLE

The solution of 3-chloroallyl thiocyanate in 1,2-dichloroethane was prepared as above and the compound was subjected to thermal rearrangement by heating to 110° C. for 12 hours but in the absence of acid. A large amount of tarry solid was formed. This solid was removed by filtration through charcoal and yielded 400 g of a clear yellow solution. GC analysis showed that the product comprised only 56 percent of 3-chloro-prop-1-enyl isothiocyanate as a mixture of trans- and cis-isomers in the ratio 1.5:1, together with 12 percent of unconverted dichloropropene, 21 percent of 1,3-bis (isothiocyanate) propenes and numerous minor impurities.

EXAMPLE 2

A solution of 3-chlorallyl thiocyanate in 1,2-dichlorethane, of concentration 24 percent by weight, prepared by the process described in Example 1, was heated with 5 mole percent of methanesulphonic acid at 115° C. for 10 hours. The resulting solution comprised a mixture of trans- and cis-isomers of 3chloro-prop-1-enyl isothiocyanate, in a yield of 91 percent based on the 3-chlorallyl thiocyanate. The overall yield of the product based on the 1,3-dichloropropene was determined by GC analysis to be 78 percent by weight.

EXAMPLE 3

A solution of 3-chlorallyl thiocyanate in 1,2-dichloroethane, of concentration 24 percent by weight, prepared by the process described in Example 1, was placed in an autoclave with 1 mole percent of p-toluenesulphonic acid. The mixture was heated to 105–110° C. for 13 hours and yielded a solution of 3-chloro-prop-1-enyl isothiocyanate as a mixture of trans- and cis-isomers in the ratio of 2.1:1, which mixed isomers comprised 83 percent of the total product.

The isothiocyanate solution was directly chlorinated with 1.2 mole equivalent of sulphuryl chloride, at −20° to 0° C., as described in our UK Patent Specification No 2305172A. The 2-chloro-5-chloromethyl thiazole hydrochloride formed was removed from the reaction mixture by filtration and amounted to an overall yield of 53 percent based on the 1,3-dichloropropene starting material.

EXAMPLES 4 TO 10

3-chloroallyl thiocyanate, prepared by reaction of 1,3-dichloropropene and sodium thiocyanate in water, was extracted into 1,1,2-trichloroethane to give a 20 percent by weight solution of the thiocyanate. The solution was heated at 110° C. for 5 to 10 hours until the conversion was completed. In Examples 5 to 10, the heating was carried out in the presence of the respective acidic material specified in the following table; in Example 4, the acidic material was omitted for comparison purposes. The yield of 3-chloro-prop-1-enyl isothiocyanate in each case is given below, together with the ratio of trans- to cis-isomer in the product.

| Example | Acidic material (mole per cent based on thiocyanate) | Yield of thiocyanate | Ratio of trans- to cis-isomers |
| --- | --- | --- | --- |
| 4 | None | 37.2% | 1.3:1 |
| 5 | 36% Hydrochloric acid (5%) | 62.8% | 2.1:1 |
| 6 | 98% Sulphuric acid (5%) | 59.4% | 2.4:1 |
| 7 | Thionyl chloride (5%) | 58.7% | 1.8:1 |
| 8 | Phosphorus oxychloride (5%) | 66.1% | 2.8:1 |
| 9 | p-Toluenesulphonic acid (5%) | 73.1% | 3.1:1 |
| 10 | Methanesulphonic acid (5%) | 75.8% | 4.0:1 |

EXAMPLES 11 TO 17

3-chloroallyl thiocyanate, prepared by reaction of 1,3-dichloropropene and sodium thiocyanate in water, was extracted into toluene to give a 30 percent by weight solution of the thiocyanate. The solution was heated under reflux for 6 to 12 hours until the conversion was completed. In Examples 12 to 17, the heating was carried out in the presence of the respective acidic material specified in the following table; in Example 11, acidic material was omitted for comparison purposes. The yield of 3-chloro-prop-1-enyl isothiocyanate in each case is given below, together with the ratio of trans- to cis-isomer in the product.

| Example | Acidic material (mole per cent based on thiocyanate) | Yield of thiocyanate | Ratio of trans- to cis-isomers |
| --- | --- | --- | --- |
| 11 | None | 44.7% | 1.6:1 |
| 12 | 36% Hydrochloric acid (5%) | 74.0% | 2.2:1 |
| 13 | 98% Sulphuric acid (5%) | 60.5% | 2.6:1 |
| 14 | Thionyl chloride (5%) | 59.1% | 1.8:1 |
| 15 | Phosphorus oxychloride (5%) | 80.3% | 4.1:1 |

| Example | Acidic material (mole per cent based on thiocyanate) | Yield of thiocyanate | Ratio of trans- to cis-isomers |
|---|---|---|---|
| 16 | p-Toluenesulphonic acid (5%) | 66.0% | 4.2:1 |
| 17 | Methanesulphonic acid (5%) | 78.9% | 4.7:1 |

What is claimed is:

1. A process for the preparation of a vinyl isothiocyanate, which process comprises contacting a halogen-substituted allyl thiocyanate, in solution and at an elevated temperature, with an acidic material which is either an acid or a halide or oxyhalide of an inorganic acid.

2. A process as claimed in claim 1, wherein the halogen-substituted allyl thiocyanate is of general formula

$NCS.CH(R_1).CH=C(R_2).Hal,$ wherein the symbols $R_1$ and $R_2$ each represents a hydrogen atom or an alkyl group containing from 1 to 3 carbon atoms and the symbol Hal represents a chlorine or bromine atom.

3. A process as claimed in claim 2, wherein the halogen-substituted allyl thiocyanate is produced by reacting a dihalogenated alkene of the general formula

$Hal.CH(R_1).CH=C(R_2).Hal,$ wherein the atoms represented by the symbols Hal may be the same or different, with an alkali metal thiocyanate or with ammonium thiocyanate.

4. A process as claimed in claim 3, wherein the dihalogenated alkene is 1,3-dichloropropene and the vinyl isothiocyanate is 3chloro-prop-1-enyl isothiocyanate.

5. A process for the preparation of a vinyl isothiocyanate of the general formula

$Hal.CH(R_1).CH=C(R_2).NCS,$ in which general formula the symbols $R_1$ and $R_2$ each represents a hydrogen atom or an alkyl group containing from 1 to 3 carbon atoms and the symbol Hal represents a chlorine or bromine group, which process comprises contacting a halogen-substituted allyl thiocyanate of the general formula

$NCS.CH(R_1).CH=C(R_2).Hal,$ in which general formula the symbols $R_1$, $R_2$ and Hal have the foregoing meanings, in solution and at an elevated temperature, with an acidic material selected from the group comprising acids and the halides and oxyhalides of inorganic acids.

6. A process as claimed in claim 5, wherein the acidic material is an acid selected from the group comprising hydrochloric acid, sulphuric acid, nitric acid, aliphatic acids of general formula $R_3.COOH$, wherein the symbol $R_3$ represents an alkyl group containing 1 to 3 carbon atoms, and organic sulphonic acids.

7. A process as claimed in claim 6, wherein the organic sulphonic acid is methanesulphonic acid or p-toluenesulphonic acid.

8. A process as claimed in claim 5, wherein the acidic material is thionyl chloride or phosphorus oxychloride.

9. A process as claimed in claim 5, wherein the amount of the acidic material is between 1 and 25 mole percent of the allyl thiocyanate.

10. A process as claimed in claim 9, wherein said amount of the acidic material is between 1 and 10 mole percent of the allyl thiocyanate.

11. A process as claimed in claim 5, wherein the contacting of the halogen-substituted allyl thiocyanate with an acidic material is carried out in solution in an aliphatic, cycloaliphatic or aromatic hydrocarbon or a chlorinated hydrocarbon.

12. A process as claimed in claim 11, wherein the solvent for said solution is heptane, cyclohexane, toluene, 1,2-dichloroethane or 1,1,2-trichlorethane.

13. A process as claimed in claim 6, wherein the contacting of the halogen-substituted allyl thiocyanate with an acidic material is carried out at a temperature within the range from 50° to 150° C.

14. A process as claimed in claim 13, wherein said temperature lies within the range from 80° to 130° C.

15. A process for the preparation of 3-chloro-prop-1-enyl isothiocyanate, which process comprises contacting 3-chlorallyl thiocyanate, in solution in a solvent selected from the group comprising heptane, cyclohexane, toluene, 1,2-dichloroethane and 1,1,2-trichlorethane at a temperature within the range from 50° to 150° C., with an acidic material selected from the group comprising acids and the halides and oxyhalides of inorganic acids.

16. A process as claimed in claim 15, wherein the acidic material is selected from the group comprising hydrochloric acid, sulphuric acid, methanesulphonic acid, p-toluenesulphonic acid, thionyl chloride and phosphorus oxychloride.

17. A process as claimed in claim 8, wherein the contacting of the halogen-substituted allyl thiocyanate with an acidic material is carried out at a temperature within the range from 50° to 150° C.

18. A process as claimed in claim 11, wherein the contacting of the halogen-substituted allyl thiocyanate with an acidic material is carried out at a temperature within the range from 50° to 150° C.

19. A process as claimed in claim 1, wherein the temperature is within the range from 50° C. to 150° C.

* * * * *